United States Patent [19]

Seido et al.

[11] Patent Number: 5,144,042
[45] Date of Patent: Sep. 1, 1992

[54] PROCESS FOR PREPARING OPTICALLY ACTIVE 3-HYDROXYPYRROLIDINE DERIVATIVES

[75] Inventors: Nobuo Seido; Yoshiki Okeda; Hidenori Kumobayashi, all of Tokyo, Japan

[73] Assignee: Takasago International Corporation, Tokyo, Japan

[21] Appl. No.: 682,273

[22] Filed: Apr. 9, 1991

[30] Foreign Application Priority Data

Apr. 11, 1990 [JP] Japan .................................. 2-93962

[51] Int. Cl.$^5$ ............................................ C07D 207/12
[52] U.S. Cl. ...................................... 548/541; 546/281
[58] Field of Search ......................................... 548/541

Primary Examiner—David B. Springer
Attorney, Agent, or Firm—Sughrue, Mion, Zinn, Macpeak & Seas

[57] ABSTRACT

A process for preparing optically active 3-hydroxypyrrolidine derivatives useful as intermediates represented by formula (III):

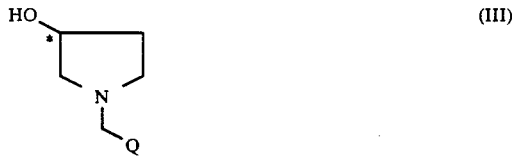

(III)

wherein Q represents a substituted or unsubstituted phenyl group; and * indicates an asymmetric carbon atom, comprising reacting an optically active 4-halo-3-hydroxybutane derivative represented by formula (I):

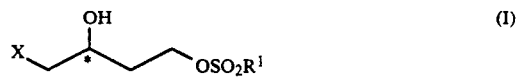

(I)

wherein * is as defined above; $R^1$ represents a lower alkyl group or a substituted or unsubstituted phenyl group; and X represents a halogen atom, with a benzylamine derivative represented by formula (II):

$H_2NCH_2Q$ (II)

wherein Q is as defined above, is disclosed. The starting compound (I) is easily available through chemical synthesis. Any complicated procedure or use of an expensive reagent is not required.

5 Claims, No Drawings

PROCESS FOR PREPARING OPTICALLY ACTIVE 3-HYDROXYPYRROLIDINE DERIVATIVES

FIELD OF THE INVENTION

This invention relates to a process for preparing optically active 3-hydroxypyrrolidine derivatives represented by formula (III) shown below which are useful as intermediates for synthesizing pharmaceuticals.

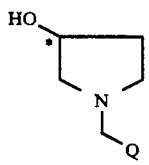

wherein Q represents a substituted or unsubstituted phenyl group; and * indicates an asymmetric carbon atom.

BACKGROUND OF THE INVENTION

Optically active 1-benzyl-3-hydroxypyrrolidine or a derivative thereof represented by formula (III) is reacted to 2,6-dimethyl-4-(m-nitrophenyl)-1,4-dihydropyridine-3,5-dicarboxylic acid-3-(1-benzyl-3-pyrrolidinyl) ester-5-methyl ester (hereinafter referred to as YM-09730), which has recently been found to have characteristic pharmacological effects, such as an effect to increase coronary blood flow when directly administered into the coronary artery. Thus, the compounds of formula (III) have been expected to be useful as starting materials for pharmaceuticals (see JP-A-61-63652 (the term "JP-A" as used herein means an "unexamined published Japanese patent application")).

3-Hydroxypyrrolidine which is structurally similar to the optically active 3-hydroxypyrrolidine derivatives of formula (III) is an industrially useful compound long known as an intermediate for pharmaceuticals and agricultural chemicals. It has conventionally been synthesized by, for example, once obtaining 1-benzyl-3-hydroxypyrrolidine and heating it in an autoclave in a hydrogen gas atmosphere in the presence of a palladium catalyst to release toluene. Other known processes for preparing 3-hydroxypyrrolidine include a process comprising reaction of 4-amino-1,2-butanediol in the presence of a metallic catalyst (see JP-A-57-56457), a process comprising decarboxylation of 4-hydroxy-L-proline in the presence of cyclohexenone (see JP-A-60-23328), and a process comprising reacting a butane derivative represented by the formula:

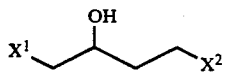

wherein $X^1$ and $X^2$, which may be the same or different, each represents an alkylsulfonyloxy group, a halogenoalkylsulfonyloxy group, an arylsulfonyloxy group, or a halogen atom, e.g., 2-hydroxy-1,4-di(methylsulfonyloxy)butane, with ammonia (see JP-A-60-104061).

Processes for synthesizing 1-benzyl-3-hydroxypyrrolidine, one of the aimed compounds of the present invention, which have been proposed to date include (1) a process comprising cyclizing dl-malic acid by reacting it with benzylamine to obtain 1-benzyl-3-hydroxysuccinic acid imide, which is then reduced with lithium aluminum hydride as described in *Synthetic Communications*, Vol. 13 (13), pp. 1117-1123 (1983); and (2) a process comprising reacting an alkyl 4-halo-3-hydroxybutyrate or an alkyl 3,4-epoxybutyrate with a benzylamine derivative to obtain a 1-benzyl-4-hydroxy-2-pyrrolidone derivative, which is then reduced with a reducing agent, e.g., lithium aluminum hydride, as described in JP-A-64-45360 and JP-A-1-207266.

From the fact that YM-09730 obtained via optically active (S)-(−)-1-benzyl-3-hydroxypyrrolidine as an intermediate is pharmacologically useful, a process for preparing (S)-(−)-1-benzyl-3-hydroxypyrrolidine has been proposed, in which optically active mandelic acid is added to a mixture of (S)-(−)-1-benzyl-3-hydroxypyrrolidine and a small proportion of by-produced (R)-(+)-1-benzyl-3-hydroxypyrrolidine which is obtained from (S)-(−)-malic acid according to the above-described process (1), to thereby crystallize a mandelic acid salt of (S)-(−)-1-benzyl-3-hydroxypyrrolidine, and the acid radical is then removed with an alkali, as disclosed in JP-A-61-63652.

However, each of the conventional processes for obtaining optically active 1-benzyl-3-hydroxypyrrolidine useful as an intermediate for pharmaceuticals involves problems. For example, naturally-occurring optically active compounds which are not easily available are used as a starting material as in the process (1); a step of cyclization followed by reduction is required, and lithium aluminum hydride which is not only difficult to handle on an industrial scale but expensive must be used as a reducing agent as in both processes (1) and (2).

In the light of these problems, it has been demanded to develop an economically advantageous process for obtaining optically active 1-benzyl-3-hydroxypyrrolidine derivatives useful as intermediates for pharmaceuticals, which process starts with an easily available optically active compound obtainable through, for example, synthetic procedures, and requires no complicated step.

SUMMARY OF THE INVENTION

The inventors have conducted extensive studies to solve the above-mentioned problems associated with conventional processes for preparing optically active 1-benzyl-3-hydroxypyrrolidine derivatives and, as a result, found that the desired compounds can be obtained with industrial advantages by cyclizing an optically active 4-halo-3-hydroxybutane derivative represented by formula (I) shown below by reaction with a benzylamine derivative and that the starting compound of formula (I) can be obtained by reducing an optically active 4-halo-3-hydroxybutyric acid ester, that is easily available through chemical synthesis in accordance with the process disclosed in JP-A-63-310847 (corresponding to U.S. Pat. No. 4,933,482 and European Patent 295,109A) by part of the present inventors, and introducing a sulfonyl group, and thus completed the present invention.

The present invention relates to a process for preparing an optically active 3-hydroxypyrrolidine derivative represented by formula (III):

wherein Q represents a substituted or unsubstituted phenyl group; and * indicates an asymmetric carbon atom, comprising reacting an optically active 4-halo-3-hydroxybutane derivative represented by formula (I):

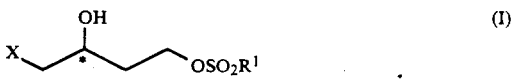

wherein * is as defined above; R¹ represents a lower alkyl group or a substituted or unsubstituted phenyl group; and X represents a halogen atom, with a benzylamine derivative represented by formula (II):

$$H_2NCH_2Q \qquad (II)$$

wherein Q is as defined above.

DETAILED DESCRIPTION OF THE INVENTION

The starting optically active 4-halo-3-hydroxybutane derivative of formula (I), though unlimited in processes for the preparation thereof, is advantageously obtained through chemical synthesis according to the following reaction scheme:

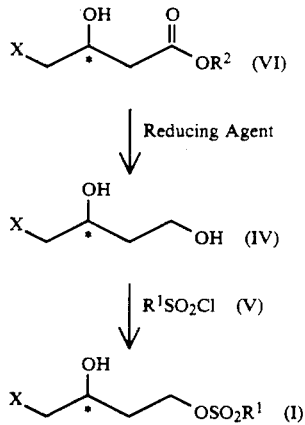

wherein R¹, X and * are as defined above; and R² represents a lower alkyl group.

The lower alkyl group as represented by R² in formula (VI) includes a straight chain or branched alkyl group having from 1 to 4 carbon atoms, e.g., a methyl group, an ethyl group, an n-butyl group, and an isobutyl group. The halogen atom as represented by X includes a chlorine atom, a bromine atom, and an iodine atom.

The compound of formula (VI) can easily be obtained according to the process disclosed in JP-A-63-310847 supra, i.e., by asymmetrically hydrogenating a γ-halo-β-keto ester represented by formula (VII):

wherein R² and X are as defined above, in the presence of a ruthenium-optically active phosphine complex as a catalyst.

The thus obtained compound of formula (VI) is reduced to obtain an optically active 4-halo-1,3-butanediol of formula (IV). Methods for reducing a carboxylic acid ester to a corresponding alcohol include, for example, the process described in R. B. Moffett, *Organic Synthesis*, Collective volume 4, pp. 834-835 (1963) and the process described in R. Adams et al., *Journal of American Chemical Society*, Volume 72, pp. 158-163 (1950). Useful reducing agents include calcium borohydride and lithium aluminum hydride, with the former being preferred from the standpoint of reaction efficiency and economy. Calcium borohydride is easily obtained by reaction between 2 equivalents of sodium borohydride and 1 equivalent of calcium chloride. This reaction is preferably carried out in a water-free condition. That is, sodium borohydride and anhydrous calcium chloride are reacted in a solvent, e.g., dried dioxane, and the compound of formula (VI) is then added thereto dropwise at −10 to 30° C., and preferably 0° to 20° C., to conduct a reduction reaction. After completion of the reaction, the reaction mixture is rendered acidic (pH 1 to 3) with an acid, e.g., a 10% hydrochloric acid solution in absolute methanol. The thus precipitated crystal is collected by filtration, freed of excess dioxane and methanol by distillation under reduced pressure at 40° C. or lower, washed with a saturated sodium chloride aqueous solution, etc., and extracted with an appropriate solvent, e.g., ethyl acetate, to recover the compound of formula (IV).

The compound of formula (IV) is then reacted with a sulfonyl compound represented by formula (V) to introduce an alkylsulfonyloxy group or an arylsulfonyloxy group selectively to the 1-positioned hydroxyl group of the compound of formula (IV) to thereby obtain an optically active compound of formula (I).

The lower alkyl group as represented by R¹ in formulae (I) and (V) includes a straight chain or branched alkyl group having from 1 to 4 carbon atoms, e.g., a methyl group and an isobutyl group. The substituted or unsubstituted phenyl group as represented by R¹ in formulae (I) and (V) includes a phenyl group, a lower alkyl-substituted phenyl group, a lower alkoxy-substituted phenyl group, and a halogen-substituted phenyl group.

Selective substitution of the hydroxyl group at the 1-position of 1,3-butanediol can be effected, for example, by the process disclosed in Y. Gao et al., *Journal of Organic Chemistry*, Vol. 53, pp. 4081-4084 (1988). That is, the compound of formula (IV) is dissolved in an organic solvent, e.g., methylene chloride, dichloroethane, diethyl ether, dioxane, and pyridine. After cooling the solution to −30° to 10° C., a base, e.g., triethylamine, dimethylaniline, pyridine, and 4-dimethylaminopyridine, is added to the solution in an amount of from 2 to 10 moles, and preferably from 2 to 3 moles, per mole of the compound of formula (IV). Then, the sulfonyl compound of formula (V) is added thereto in an amount of from 1 to 1.2 mole per mole of the compound of formula (IV), and the mixture is allowed to react with stirring under temperature and time conditions selected according to the reaction rate of the compound (IV). After completion of the reaction, the reaction mixture is made acidic (pH 1 to 2) with an acid, e.g., a 5% hydrochloric acid aqueous solution, washed with a saturated sodium hydrogencarbonate aqueous solution, a saturated sodium chloride aqueous solution, etc., and freed of the excess solvent by distillation to obtain the compound of formula (I).

The resulting compound of formula (I) is dissolved in an alcohol, e.g., methanol, ethanol, and butanol, and to the solution is added an inorganic base, e.g., potassium carbonate, sodium carbonate, and lithium carbonate, in an approximately equimolar amount to the compound (I) or an organic base, e.g., triethylamine, pyridine, and dimethylaniline, in an amount of from an equimolar amount to twice the moles of the compound (II). Then, the benzylamine derivative represented by formula (II) is added thereto in an amount of from 1 to 2 moles, and preferably from 1.1 to 1.2 mole, per mole of the compound (I), followed by heating at reflux for 5 to 20 hours.

The substituted or unsubstituted phenyl group as represented by Q in formulae (II) and (III) includes a phenyl group, a lower alkyl-substituted phenyl group, a lower alkoxy-substituted phenyl group, and a halogen-substituted phenyl group.

Examples of particularly preferred benzylamine derivatives are benzylamine, p-methoxybenzylamine, 2,4-dimethoxybenzylamine, and 3,4,5-trimethoxybenzylamine.

After completion of the reaction, the excess solvent is removed from the reaction mixture by distillation. The residue is subjected to liquid separation by using a solvent, e.g., water-ethyl acetate, and the resulting organic layer is further worked-up by, for example, distillation to obtain the desired optically active 3-hydroxypyrrolidine derivative of formula (III).

The present invention is now illustrated in greater detail by way of Examples, but it should be understood that the present invention is not deemed to be limited thereto. All the percents, parts, and ratios are by weight unless otherwise specified.

In Examples, $^1$H-NMR spectra were determined with AM-400 (400 MHz) manufactured by Bruker Inc. (internal standard: tetramethylsilane), and optical rotations were measured with DIP-4 manufactured by JASCO Inc.

EXAMPLE 1

Preparation of (3S)-4-Chloro-1,3-butanediol (IV)

In 100 ml of dried 1,4-dioxane, 148.8 g (3.93 mole) of sodium borohydride and 218.3 g (1.93 mole) of anhydrous calcium chloride were reacted at room temperature for 15 hours. To the resulting calcium borohydride was added dropwise a mixed solution of 200 g (1.3 mole) of methyl (3S)-4-chloro-3-hydroxybutyrate and 200 ml of 1,4-dioxane at 15° C. over a period of 4 hours. The mixture was stirred at 15° C. for 15 hours, and 502 g (15.7 mole) of methanol was added dropwise thereto at that temperature over 4 hours. To the reaction mixture was added 2500 ml of a 10% hydrochloric acid solution in methanol at 20° C., and the precipitated crystal was removed by filtration. The filtrate was concentrated at 40° C. under reduced pressure (5 to 10 mmHg). To the concentrate was added dropwise 870 ml of a saturated sodium chloride aqueous solution, and the precipitated crystal was removed by filtration. The filtrate was extracted three times with 3000 ml portions of ethyl acetate, and the extract was dried over anhydrous magnesium sulfate and concentrated under reduced pressure at 40° C. to obtain 160 g (yield: 97%) of the titled compound.

$^1$H-NMR (CDCl$_3$) δ ppm: 1.75-1.85 (m, 2H), 3.58 (dd, 2H), 3.86 (m, 2H), 4.07 (m, 1H)

EXAMPLE 2

Preparation of (3S)-4-Chloro-3-hydroxy-1-methylsulfonyloyxbutane (I)

A solution of 5 g (40 mmole) of (3S)-4-chloro-1,3-butanediol as obtained in Example 1 in 50 ml of methylene chloride was cooled to −30° C. on a dry ice-acetone bath, and 11 ml (80 mmole) of triethylamine was added dropwise to the solution over 20 minutes. A solution of 4.58 g (40 mmole) of methanesulfonyl chloride in 100 ml of methylene chloride was then added dropwise thereto over 1 hour, followed by stirring for 30 minutes. The resulting reaction mixture was poured into 200 ml of ice-water for liquid separation. The organic layer was washed successively with 150 ml of 1N hydrochloric acid, 200 ml of a saturated sodium hydrogencarbonate aqueous solution and 200 ml of a saturated sodium chloride aqueous solution, dried over anhydrous magnesium sulfate, and then freed of the solvent by distillation to obtain 3.10 g of a concentrate. $^1$H-NMR determination revealed that the resulting concentrate contained 87.8% (yield: 36.8%) of desired (3S)-4-chloro-3--hydroxy-1-methylsulfonyloxybutane.
$^1$H-NMR (CDCl$_3$) δ ppm: 1.90-2.10 (m, 2H), 3.05 (s, 3H), 3.60 (m, 2H), 3.90 (m, 2H), 4.45 (m, 1H)

EXAMPLE 3

Preparation of (3R)-4-Chloro-3-hydroxy-1-p-tolylsulfonyloxybutane (I)

A solution of 5 g (40 mmole) of (3R)-4-chloro-1,3-butanediol in 30 ml of methylene chloride, said (3R)-4-chloro-1,3-butanediol being obtainable in a similar manner as in Example 1 starting from methyl (3R)-4-chloro-3-hydroxybutyrate, was cooled to −20° C. on a dry ice-acetone bath, and 8.13 g (80 mmole) of triethylamine was added dropwise thereto over 30 minutes. A solution of 7.66 g (40.2 mmole) of p-toluenesulfonyl chloride in 100 ml of methylene chloride was added dropwise thereto over 50 minutes. After returning to room temperature, the mixture was stirred for 20 hours. The reaction mixture was poured into 200 ml of ice-water for liquid separation. The organic layer was washed successively with 100 ml of 1N hydrochloric acid, 100 ml ×2 of a saturated sodium hydrogencarbonate aqueous solution and 100 ml of a saturated sodium chloride aqueous solution and then freed of the solvent by distillation to obtain 7.8 g of a concentrate. The concentrate was purified by silica gel column chromatography (hexane/ethyl acetate=2:1 by volume) to obtain 6.1 g (yield: 54%) of the titled compound. $^1$H-NMR (CDCl$_3$) δ ppm: 1.78-2.00 (m, 2H), 2.46 (s, 3H), 3.45-3.65 (dd, 2H), 3.95 (m, 1H), 4.20 (m, 2H), 7.40 (d, 2H), 7.80 (d, 2H)

EXAMPLE 4

Preparation of (3S)-4-Chloro-3-hydroxy-1-methylsulfonyloxybutane (I)

A solution of 5 g (40 mmole) of (3S)-4-chloro-1,3-butanediol as obtained in Example 1 in 50 ml of methylene chloride was cooled to −30° C. on a dry ice-acetone bath, and 9.48 g (80 mmole) of pyridine was added dropwise to the solution over 30 minutes. To the solution was added dropwise a solution of 4.58 g (40 mmole) of methanesulfonyl chloride in 50 ml of methylene chloride over 1 hour, followed by stirring at room temperature for 15 hours. The resulting reaction mixture was poured into 150 ml of ice-water for liquid separation. The organic layer was washed successively with 150 ml of 1N hydrochloric acid, 100 ml of a saturated sodium hydrogencarbonate aqueous solution, and 100 ml ×2 of a saturated sodium chloride aqueous solution, and dried over anhydrous magnesium sulfate. The solvent was removed by distillation to obtain 3.21 g (yield: 37.2%) of a concentrate.

EXAMPLE 5

Preparation of (3S)-4-Chloro-3-hydroxy-1-methylsulfonyloxybutane (I)

To a solution of 5 g (40 mmole) of (3S)-4-chloro-1,3-butanediol as obtained in Example 1 in 50 ml of dioxane was added dropwise 6.4 ml (80 mmole) of pyridine under ice-cooling (0°-5° C.) over 30 minutes. A solution of 4.58 g (40 mmole) of methanesulfonyl chloride in 50 ml of dioxane was then added dropwise thereto over 1 hour, followed by stirring at room temperature for 15 hours. The reaction mixture was poured into 150 ml of ice-water for liquid separation. The organic layer was washed successively with 150 ml of 1N hydrochloric acid, 100 ml of a saturated sodium hydrogencarbonate aqueous solution, and 100 ml ×2 of a saturated sodium chloride aqueous solution, dried over anhydrous magnesium sulfate, and freed of the solvent by distillation to obtain 6.5 g of a concentrate. $^1$H-NMR determination revealed that the concentrate contained 92% of the titled compound (yield: 78%).

EXAMPLE 6

Preparation of (3S)-1-Benzyl-3-hydroxypyrrolidine (III)

To 2 g (10.6 mmole) of (3S)-4-chloro-3-hydroxy-1-methylsulfonyloxybutane as obtained in Example 4 were added 1.18 ml (10.7 mmole) of benzylamine, 1.34 g (12.72 mmole) of sodium carbonate, and 20 ml of ethanol, and the mixture was allowed to react at reflux for 5 hours. After cooling, the ethanol was removed by distillation under reduced pressure, and to the residue were added 20 ml of ethyl acetate and 10 ml of water, followed by stirring. After liquid separation, the organic layer was dried over anhydrous magnesium sulfate, and the ethyl acetate was removed by distillation. The residue was distilled to obtain 1.76 g (yield: 94%) of the titled compound as a fraction having a boiling point of 105°-110° C. (0.9 mmHg). $^1$H-NMR (CDCl$_3$) δ ppm: 1.75 (m, 1H), 2.20 (m, 1H), 2.35 (m, 1H), 2.50 (br, 1H), 2.60 (m, 1H), 2.70 (m, 1H), 2.90 (m, 1H), 3.70 (s, 2H), 4.32 (m, 1H), 7.30 (s, 2H)

[α]$_D^{25}$: −3.58° (c=5, methanol)

The optical purity of the product was found to be 95.2%ee as calculated from the data [α]$_D^{25}$:−3.77° for 100%ee in Bhat. K.L. et al., *Synthetic Communications*, Vol. 15, p. 587 (1985).

EXAMPLE 7

Preparation of (3R)-1-Benzyl-3-hydroxypyrrolidine (III)

To 2 g (7.18 mmole) of (3R)-4-chloro-3-hydroxy-1-p-tolylsulfonyloxybutane as obtained in Example 3 were added 0.78 g (7.3 mmole) of benzylamine, 0.92 g (8.68 mmole) of sodium carbonate, and 20 ml of ethanol, and the mixture was allowed to react at reflux for 7 hours. After cooling, ethanol was removed by distillation under reduced pressure. To the residue were added 100 ml of ethyl acetate and 50 ml of water, followed by stirring. After liquid separation, the organic layer was dried over anhydrous magnesium sulfate, and the solvent was removed by distillation. The residue was distilled under reduced pressure to obtain 1.1 g (yield: 86.5%) of the titled compound.

As described above, the present invention provides a process for advantageously obtaining optically active 3-hydroxypyrrolidine derivatives useful as intermediates for synthesizing pharmaceuticals, characterized in that an optically active 4-halo-3-hydroxybutane derivative which can be easily synthesized is cyclized by a benzylamine derivative. As involving no complicated procedures as in conventional processes and also being economically advantageous, the process of the invention is industrially excellent.

While the invention has been described in detail and with reference to specific examples thereof, it will be apparent to one skilled in the art that various changes and modifications can be made therein without departing from the spirit and scope thereof.

What is claimed is:

1. A process for preparing an optically active 3-hydroxypyrrolidine derivative represented by formula (III):

wherein Q represents a substituted or unsubstituted phenyl group; and * indicates an asymmetric carbon atom, comprising reacting an optically active 4-halo-3-hydroxybutane derivative represented by formula (I):

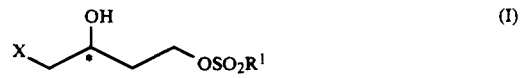

wherein * is defined above, R$^1$ represents a lower alkyl group or a substituted or unsubstituted phenyl group; and X represents a halogen atom, with a benzylamine derivative represented by formula (II), said reacting being in an alcohol solvent in the presence of a base:

N$_2$NCH$_2$Q    (II)

wherein Q is as defined above.

2. A process for preparing an optically active 3-hydroxypyrrolidine derivative represented by formula (III):

wherein Q represents a substituted or unsubstituted phenyl group; and * indicates an asymmetric carbon atom, comprising reacting an optically active 4-halo-1,3-butanediol represented by formula (IV):

wherein * is as defined above; and X represents a halogen atom, with a sulfonyl compound represented by formula (V), wherein a solution of the optically active 4-halo-1,3-butanediol represented by formula (IV) dissolved in an organic solvent selected from the group consisting of halogenated hydrocarbons, ethers, and pyridine, is mixed with a base and the sulfonyl compound represented by formula (V) at −30° to 10° C.:

   (V)

wherein $R^1$ represents a lower alkyl group or a substituted or unsubstituted phenyl group, to obtain an optically active 4-halo-3-hydroxybutane derivative represented by formula (I):

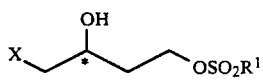   (I)

wherein $R^1$, X, and * are as defined above; and reacting the compound represented by formula (I) with a benzylamine derivative represented by formula (II):

   (II)

wherein Q is as defined above.

3. A process for preparing and optically active 3-hydroxypyrrolidine derivative represented by formula (III):

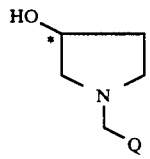   (III)

wherein Q represents a substituted or unsubstituted phenyl group; and * indicates an asymmetric carbon atom, comprising reducing an optically active 4-halo-3-hydroxybutyric acid ester represented by formula (VI) with calcium borohydride in dried dioxane under water-free conditions at from −10° to 30° C.:

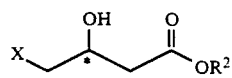   (VI)

wherein * is as defined above; $R^2$ represents a lower alkyl group; and X represents a halogen atom, to obtain an optically active 4-halo-1,3-butanediol represented by formula (IV):

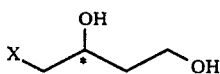   (IV)

wherein X and * are as defined above, reacting the compound represented by formula (IV) with a sulfonyl compound represented by formula (V), wherein a solution of the optically active 4-halo-1,3-butanediol represented by formula (IV) dissolved in an organic solvent selected from the group consisting of halogenated hydrocarbons, ethers, and pyridine, is mixed with a base and the sulfonyl compound represented by formula (V) at −30° to 10° C.:

   (V)

wherein $R^1$ represents a lower alkyl group or a substituted or unsubstituted phenyl group, to obtain an optically active 4-halo-3-hydroxybutane derivative represented by formula (I):

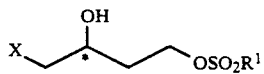   (I)

wherein $R^1$ X and * are as defined above; and reacting the compound represented by formula (I) with a benzylamine derivative represented by formula (II):

   (II)

wherein Q is as defined above.

4. The process of claim 2, wherein the sulfonyl compound represented by formula (V) is added in an amount of up to about 1.2 mole per mole of the compound of formula (IV).

5. The process of claim 3, wherein the sulfonyl compound represented by formula (V) is added in an amount of up to about 1.2 mole per mole of the compound of formula (IV).

* * * * *